(12) United States Patent
Sremcevic

(10) Patent No.: US 11,484,688 B2
(45) Date of Patent: Nov. 1, 2022

(54) MINIMALLY INVASIVE CATHETER

(71) Applicant: Univerzitet U Beogradu, Belgrade (RS)

(72) Inventor: Bosko Sremcevic, Belgrade (RS)

(73) Assignee: UNIVERZITET U BEOGRADU, Belgrade (RS)

( * ) Notice: Subject to any disclaimer, the term of this patent is extended or adjusted under 35 U.S.C. 154(b) by 0 days.

(21) Appl. No.: 17/423,850

(22) PCT Filed: Jan. 21, 2019

(86) PCT No.: PCT/RS2019/000004
§ 371 (c)(1),
(2) Date: Jul. 16, 2021

(87) PCT Pub. No.: WO2020/153860
PCT Pub. Date: Jul. 30, 2020

(65) Prior Publication Data
US 2022/0040449 A1 Feb. 10, 2022

(51) Int. Cl.
*A61M 25/00* (2006.01)
*A61M 25/01* (2006.01)
*A61M 25/10* (2013.01)

(52) U.S. Cl.
CPC ...... *A61M 25/0097* (2013.01); *A61M 25/007* (2013.01); *A61M 25/0017* (2013.01);
(Continued)

(58) Field of Classification Search
CPC .......... A61M 25/0119; A61M 25/0097; A61M 25/0017; A61M 25/007;
(Continued)

(56) References Cited

U.S. PATENT DOCUMENTS 3,053,257 A * 9/1962 Birtwell ............. A61M 25/0119
604/97.01
3,583,391 A * 6/1971 Cox ................... A61M 25/0111
600/585
(Continued)

FOREIGN PATENT DOCUMENTS

EP 0539084 A1 4/1993
WO WO-2005102435 A1 * 11/2005 ........ A61M 25/0119

*Primary Examiner* — Adam Marcetich
(74) *Attorney, Agent, or Firm* — The Watson IP Group, PLC; Jovan N. Jovanovic

(57) ABSTRACT

Minimally invasive catheter relates to the field of eversible catheters. It is primarily intended for use as a urinary catheter, but is also usable in other fields. As a urinary catheter this minimally invasive catheter 1 used as an indwelling or intermittent catheter with transurethral or suprapubic approach. This catheter has specific technical solution for eversible motion where tubular membrane 2, attached between distal part 36*a* of the handle 36 and distal part 3*a* of the inner tube 3, can in one case free slide between these two parts and in another be fixed to form hermetically sealed space 14. Free sliding of membrane ensures eversible principle of motion during placement and withdrawal of the catheter 1. Fixation of membrane allows a formation of hermetically sealed space 14 with fluid to make catheter surface smoother and softer, and a balloon 33 to hold catheter 1 in place for prolonged period of time. Thus, present invention provides a urinary catheter that enables the reduced incidence of complications arising due to its application.

11 Claims, 11 Drawing Sheets

(52) U.S. Cl.
CPC . *A61M 25/0119* (2013.01); *A61M 2025/0004* (2013.01); *A61M 2025/1065* (2013.01); *A61M 2025/1075* (2013.01); *A61M 2210/1085* (2013.01)

(58) Field of Classification Search
CPC .. A61M 2025/0004; A61M 2025/1065; A61M 2025/1075; A61M 2210/1085
See application file for complete search history.

(56) References Cited

U.S. PATENT DOCUMENTS

| | | | | |
|---|---|---|---|---|
| 3,908,663 | A * | 9/1975 | Viek | A61M 25/0119 600/581 |
| 3,911,927 | A * | 10/1975 | Rich | A61M 25/0122 604/271 |
| 4,863,440 | A * | 9/1989 | Chin | A61M 25/104 604/920 |
| 4,871,358 | A * | 10/1989 | Gold | A61M 25/0119 604/271 |
| 5,387,193 | A | 2/1995 | Miraki | |
| 5,458,573 | A * | 10/1995 | Summers | A61M 25/0119 604/101.04 |
| 6,007,521 | A | 12/1999 | Bidwell | |
| 9,463,035 | B1 * | 10/2016 | Greenhalgh | A61B 17/22031 |
| 2006/0047222 | A1 * | 3/2006 | Heuser | A61M 25/0105 600/585 |
| 2007/0123798 | A1 * | 5/2007 | Rahamimov | A61B 1/00135 600/564 |
| 2013/0060234 | A1 * | 3/2013 | Besser | A61M 25/10 604/509 |
| 2014/0107610 | A1 | 4/2014 | Witte | |
| 2015/0051631 | A1 * | 2/2015 | Gould | A61B 17/0293 606/192 |
| 2015/0142045 | A1 * | 5/2015 | Bacich | A61F 2/0027 606/193 |
| 2016/0278747 | A1 * | 9/2016 | Chin | A61B 10/0291 |
| 2017/0265724 | A1 * | 9/2017 | Lichtenstein | A61B 1/00135 |
| 2017/0360475 | A1 | 12/2017 | Chin et al. | |
| 2018/0125510 | A1 * | 5/2018 | Chin | A61B 17/3207 |
| 2019/0000429 | A1 * | 1/2019 | Magana | A61B 17/3421 |
| 2019/0126010 | A1 * | 5/2019 | Sama | A61M 25/1002 |
| 2019/0133627 | A1 * | 5/2019 | Wallace | A61B 17/320725 |
| 2019/0290475 | A1 * | 9/2019 | Chin | A61B 17/12136 |
| 2020/0008835 | A1 * | 1/2020 | Kelly | A61B 17/320758 |
| 2020/0170668 | A1 * | 6/2020 | Zilla | A61B 17/22032 |
| 2020/0205795 | A1 * | 7/2020 | Chin | A61M 25/1006 |

* cited by examiner

CROSS-SECTION B-B

CROSS-SECTION C-C

CROSS-SECTION D-D

DETAIL A

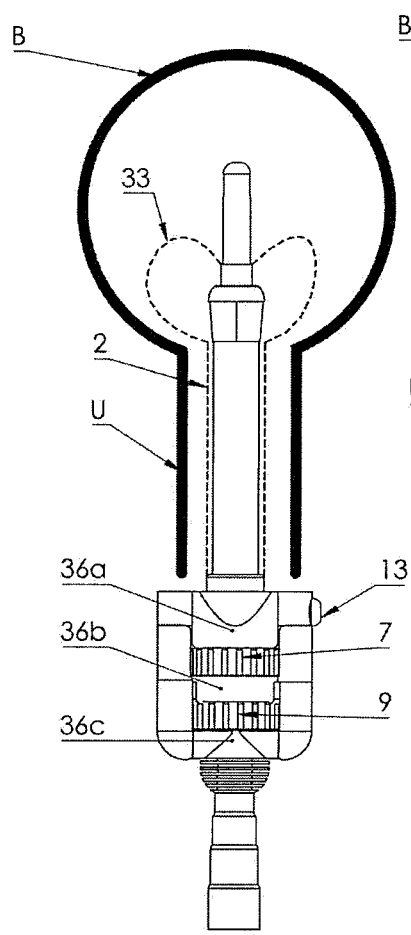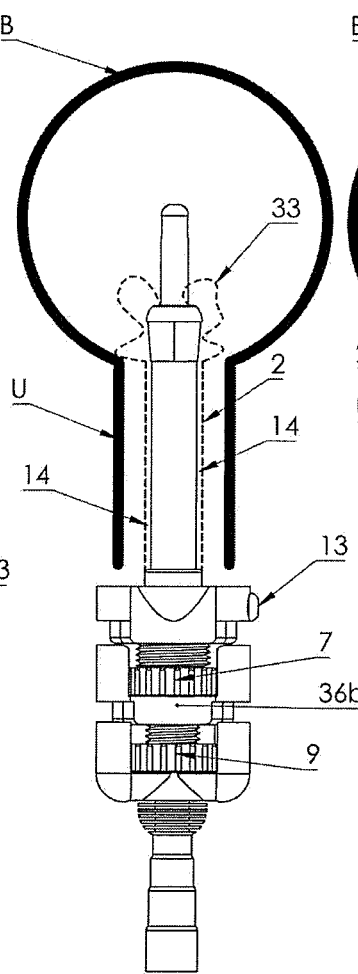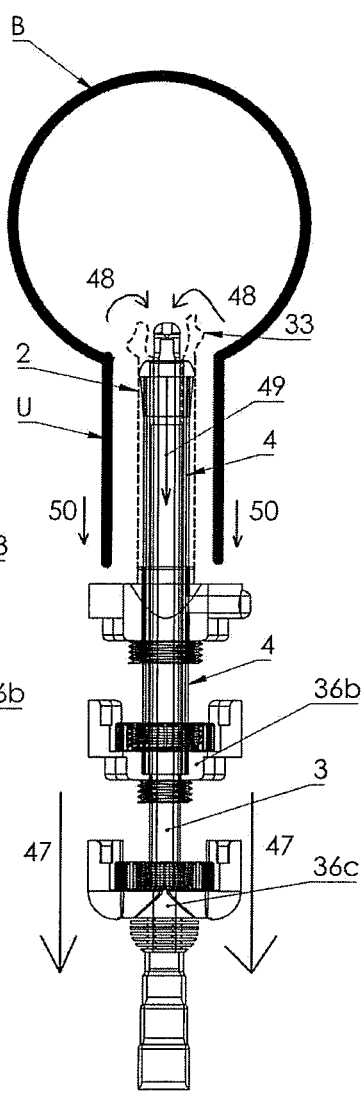
Fig. 14
Fig. 15
Fig. 16

DETAIL B

MINIMALLY INVASIVE CATHETER

TECHNICAL FIELD

The present invention relates to the field of catheters, specifically to eversible catheters. It is primarily intended for use as a urinary catheter, but it can also be used in other surgical and non-surgical medical fields. As a urinary catheter, this minimally invasive catheter can be used as an indwelling or intermittent catheter with transurethral or suprapubic approach.

TECHNICAL PROBLEM

Catheter is a flexible tube which can be inserted through a narrow opening into a body cavity for the drainage of body fluids, but it can also be used for diagnostic or therapeutic reasons.

Urinary catheters are most commonly used in subjects with impaired bladder function, incontinence or urine retention. Urinary catheters can be used as intermittent or indwelling catheters. Intermittent catheterization with high standards of cleanliness is the optimal procedure for managing urinary retention, with relatively low rate of complications. For this use, a flexible tube is inserted through urethra until urine starts flowing, and when the urine flow ceases, the catheter can be removed.

In patients where intermittent catheterization is not possible, an indwelling catheter has to be used. Indwelling catheter has a part in the form of a balloon or a similar shape, which serves to hold catheter in place for a long time. Catheterization can be for short-term usage (less than 30 days) or long-term usage (more than 30 days).

Currently, the most widely used catheter has been Foley catheter, invented more than 80 years ago. Foley catheter is indwelling catheter containing a balloon. The most commonly used size of catheter is from 11 to 16 Fr.

There is a high rate of complications related to the use of indwelling catheters. Specifically, the complications related to the use of urinary catheter are mainly a result of entering and retention of bacteria in the sterile parts of the urinary tract or damage of the urinary tract epithelial barrier. There are many other factors that lead to infections. Urinary tract infections are the most common hospital incurred infections. Foley catheter is responsible for nearly 70% of all hospital incurred urinary tract infections. The economic impact of these complications is enormous.

The reasons for such a high rate of complications may be explained by the following. Namely, it takes a lot of time to perform all the steps in order to meet the hygienic standards before placing the catheter and medical practitioners must make an effort to achieve them. However, there are frequent failures in practice. Despite the use of gloves, and other steps in order to meet the hygienic standards, parts of catheter which pass through urethra in the urinary bladder must be held with hands and frequently are being contaminated with bacteria from external environment before and during the process of placement the catheter.

The urethra, especially a part near the meatus and periurethral skin of healthy people, is colonized with bacteria. These bacteria are physiological microflora of that area, but their introduction into the bladder leads to infections. Any contact of the catheter tip with the meatus of urethrae, periurethral skin or even distal part of the urethra causes contamination of the catheter, thus infecting the sterile urinary bladder. Standard catheters that are used in medical practice currently very often enter these bacteria in the urinary bladder.

In addition, prolonged contact and friction, while placing and having in place catheter, leads to damage of the epithelial barrier—thus facilitating further entrance of bacteria into the body, and causing pain. Damage of the epithelium makes catheter placement difficult and painful which leads to narrowing of the urethra, urethral injury, blood infection, even sepsis. Standard catheters often lead to damage of the epithelium, which opens an entry site for infections.

The disadvantage of the indwelling catheters having balloons, related to catheter withdrawal, is called a "creep" phenomenon, which may cause the balloon not to collapse completely. Moreover, this protuberance at balloon region, during catheter withdrawal can damage the surrounding tissue.

Additionally, side flow of urine between catheter walls and urethra can occur, and produce significant hygiene problems. The surface of the catheter must be smooth, to prevent the deposition of bacterial biofilm, but also soft, to prevent epithelial damage.

These are some of the major problems regarding to use of catheters which are currently widely used. The minimally invasive catheter as described in the present disclosure aims to solve all the above-mentioned problems.

BACKGROUND

Recently, several solutions for an eversible catheter or similar devices have been disclosed, which are based on the eversible rolling membrane principle during placement.

U.S. Pat. No. 3,053,257 discloses a catheter having an elongated body for insertion into a tube, and a drainage passage therethrough, the distal end of the body having a drainage eye communication with the drainage passage and having a sleeve enveloping the major portion of the elongated body. The sleeve includes a balloon section. The sleeve is peelingly removed from the urethra following the withdrawal of the body. This is the catheter with eversible motion, with sleeve which is with both ends attached to the outer surface of the body. Space between sleeve and the body can be filed with fluid and form chamber with a balloon as a part of it. The eversible principle of motion is possible only at short distance. Thus, U.S. Pat. No. 3,053,257 discloses the balloon that exists between urethra wall and the body even during the withdrawal of the catheter, causing the discomfort for the patient.

U.S. Pat. No. 3,583,391 describes a medical instrument for positioning an elongated sac or catheter in a patient's urethra for urinary drainage or bacterial sampling. It discloses that the first centimeter of the distal area of the urethra often contains a high bacterial count, while the areas of the urethra nearer the bladder usually contain few bacteria or may be sterile. Thus, the invention aims to solve the problem of insertion of catheter along the entire length of urethra into bladder without transferring bacteria from the distal to the proximal areas of the urinary tract. However, the disadvantage of the instrument as disclosed is that the elongated sac can be screwed during the insertion of the catheter and it cannot be used for prolonged period of time.

U.S. Pat. No. 3,908,663 discloses a catheter comprising a disc or plate, which is provided with an aperture, within which there is a semirigid catheter tube. The forward portion of the catheter is supported within a flexible tubular envelope which terminates at its rearward end in longitudinal bands or straps. In addition, the catheter tube is provided with apertures through which bands are threaded.

The disadvantage of this invention is that due to apertures of the catheter tube, leak of the urine through them is possible. In addition, presence of disc or plate which naturally can rotate may cause twisting of the membrane and the bands.

In another embodiment disclosed in U.S. Pat. No. 3,908,663, there is an outer tube and inner tube. The tubular sleeve is semi-rigid and completely surrounded by flexible tubular envelope. The envelope is by both ends attached to the plates, which serve as a handle. In this embodiment, the envelope is also attached to the inner tube.

U.S. Pat. No. 4,871,358 discloses a medical catheter being an inversionary tube which is inwardly folded upon itself to provide a telescoping tube assembly having inner and outer tubular portions of variable length. The reduced trauma and the reduced pain, according to the invention described in U.S. Pat. No. 4,871,358, is achieved by eversible motion of the tube.

DISCLOSURE OF THE INVENTION

Minimally invasive catheter according to the present invention is a urinary catheter which can be used as an intermittent or indwelling catheter, for transurethral or suprapubic use. It is primarily intended for use as a urinary catheter, but it can also be used in other surgical and non-surgical medical fields. Minimally invasive catheter aims to reduce the incidence of complications related to use of urinary catheters. This is achieved by providing a catheter comprising inner and outer tube, tubular membrane attached to the handle and the inner tube, and allowing formation of hermetically sealed space containing balloon that may be filled up with fluid.

Before the placement of the catheter, tubular membrane 2 and the distal part 3a of the inner tube 3, as parts of the catheter which are in direct contact with urethra and urinary bladder, are protected from the contamination with bacteria from external environment by being placed inside the outer tube 4. This prevents contamination of these parts related to potential mistakes, which could be made before insertion of the catheter (hygienic procedures).

Tubular membrane 2 of the minimally invasive catheter is attached between the distal part 36a of the handle 36 and the distal part 3a of the inner tube 3. Tubular membrane 2 may freely slide between these two parts, but may also be fixed to form hermetically sealed space. Handle 36 of the catheter 1 as disclosed in the present application, comprises a distal part 36a of the handle 36, a medial part 36b of the handle 36 and a proximal part 36c of the handle 36 which are detachable connected. Distal part 36a of the handle 36 may slide along the outer tube 4. Body 3b of the inner tube 3 may slide through outer tube 4. Consequently, the tubular membrane 2 may slide between distal part 36a of the handle 36 and the distal part 3a of the inner tube 3 along and through the outer tube 4 and ensures eversible principle of motion during placement and withdrawal of the catheter. Eversible principle of motion of tubular membrane 2 during catheter insertion prevents transport of bacteria from the region around the meatus of urethra and distal part of urethra to urinary bladder, as well as reduces sliding friction, pain and trauma of epithelium of the urethra. By eversible principle of motion during catheter withdrawal, the balloon 33 of minimally invasive catheter passes through the rounded tip 5 of the outer tube 4 and "creep" phenomenon of semi-extinguished balloon is prevented.

In one embodiment, the proximal part 36c of the handle 36, the medial part 36b of the handle 36 and the distal part 36a of the handle 36 are assembled together, tightly engaged and secured with a nut 7 of the medial part 36b of the handle 36 and a nut 9 of the proximal part 36c of the handle 36. As a result, the tubular membrane 2 is fixed between handle 36 of the outer tube 4 and distal part 3a of the inner tube 3. Fixation of the tubular membrane 2 allows a formation of hermetically sealed space 14, which is formed by the surfaces of the distal part 36a of the handle 36, tubular membrane 2, body 3b of the inner tube 3, proximal part 36c of the handle 36 and medial part 36b of the handle 36. This hermetically sealed space 14 can be inflated with fluid through the hole 13 of the handle 36. Fluid can be injected with the syringe, and the hole 13 of the handle 36 may be equipped with a valve to maintain the fluid pressure after injection. This space filled with fluid will make catheter surface softer and smoother. This improves fitting of catheter surfaces on urethra walls, prevents side flow of urine between catheter surface and urethral epithelium and prevents biofilm forming. Also, tubular membrane 2 has an enlargement of the tubular membrane 2 in the shape of a balloon 33, which can hold a catheter in place for prolonged period of time.

The rounded tip 5 of the outer tube 4, as a leading part of catheter 1 during insertion, may have a larger diameter when compared with the diameter of the outer tube 4. When hermetically sealed space 14 is inflated it must have larger diameter than rounded tip 5 of the outer tube 4. It cannot have an equal diameter, because that would block eversible principle of motion of the tubular membrane 2. In addition, tip has rounded surface for an easier passage of the catheter through the urethra and easier rolling of membrane during eversible motion.

The catheter 1, according to the present invention, contains protrusions (20a, 20b, 24a, 24b) and channels (15a, 15b, 19a, 19b) that prevent twisting of tubular membrane and provide secure urine flow of the catheter. The inner tube 3 containing the lumen for urine flow passes through the entire length of the catheter.

The catheter 1, according to the present invention, provides the following advantages: prevention of contamination of the catheter before the placement, but also prevention of the dissemination of bacteria into sterile parts of urinary tract during the placement, secured flow of urine (as inner tube with lumen extends along the entire length of the catheter), reduced sliding friction during the placement and withdrawal of the catheter, reduced damage of the epithelium (due to presence of the fluid film around flexible parts, which makes the surface of the catheter 1 smoother and softer), prevention of the "creep" phenomenon, prevention of twisting of the tubular membrane during the insertion of the catheter, easier passage of the catheter through the urethra and overall, improved comfort for the patient.

This contributes to the reduced incidence of usual complications related to the use of the urinary catheter, such as urethritis, cystitis, urethral injury, blood Infection, bacteriuria, narrowing of the urethra, etc.

BRIEF DESCRIPTION OF DRAWINGS

FIG. 14 shows the catheter with its internal parts which is fixed in place with inflated balloon.

FIG. 15 shows the catheter with its internal parts during the initiation of the catheter removal.

FIG. 16 shows the catheter with its internal parts during removal progression.

DETAILED DESCRIPTION OF THE PREFERRED EMBODIMENTS

Figure 1:
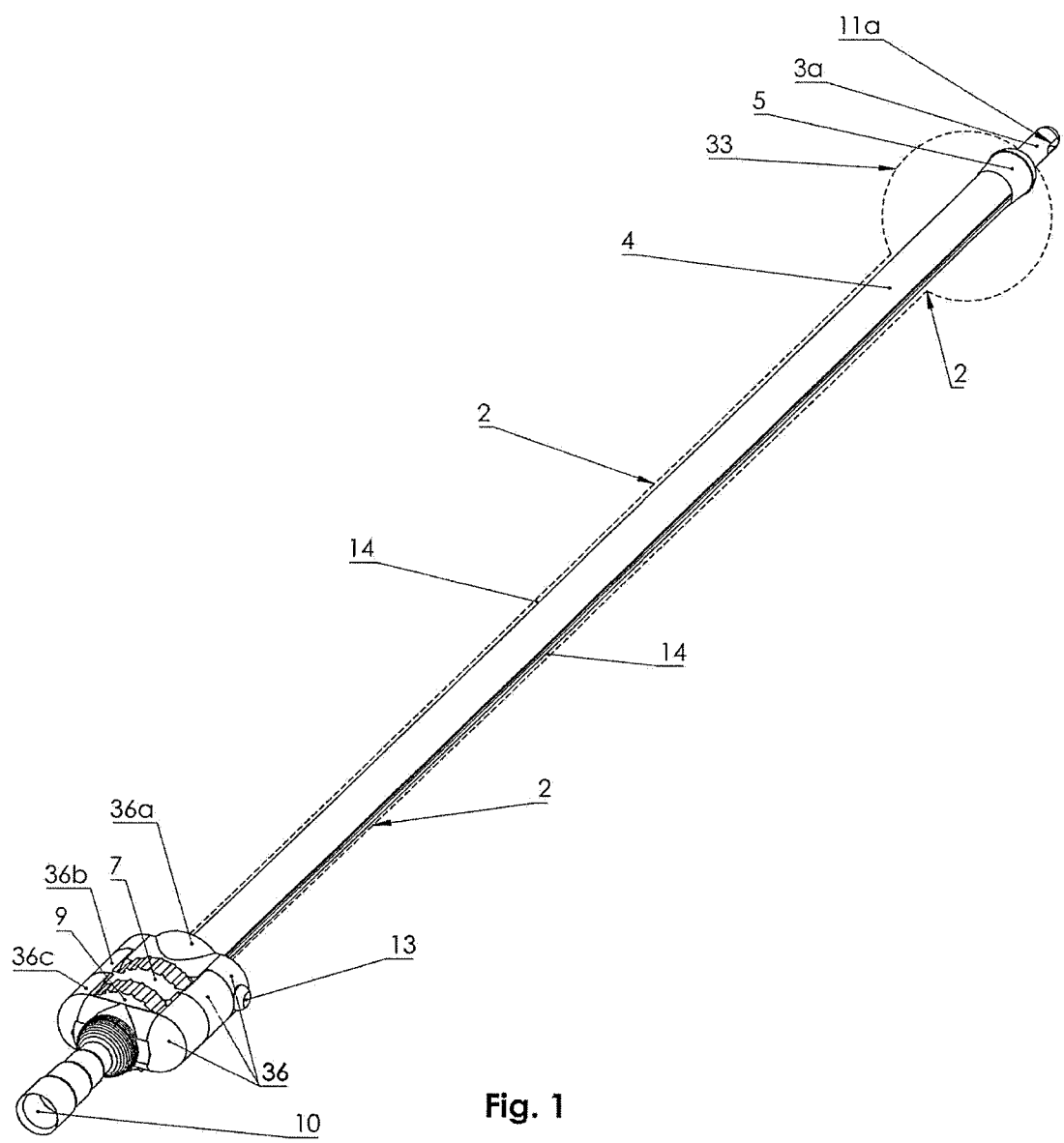
FIG. 1 is a perspective view of the catheter.
Figure 2:
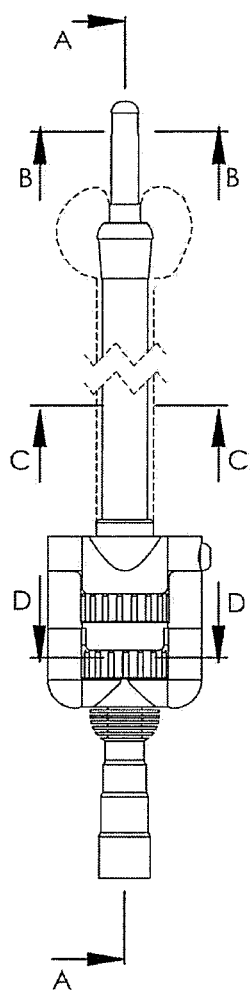
FIG. 2 is a top view of the catheter along main axis with represented position of longitudinal cross-section line A-A and positions of transversal cross-section lines B-B, C-C, D-D.

The outer tube 4 and the inner tube 3 are sufficiently flexible for easily passing curvatures of the urethra.

The catheter according to the present invention includes a distal part 36a of the handle 36, tubular membrane 2, distal part 3a of the inner tube 3, outer tube 4, rounded tip 5 of the outer tube 4, medial part 36b of the handle 36, nut 7 of the medial part 36b of the handle 36, proximal part 36c of the handle 36, nut 9 of the proximal part 36c of the handle 36, the proximal opening 10 of the catheter 1 that is attachable to urine bags, or used for access to the urinary tract or other body cavities.

The distal part 3a of the inner tube 3 has lateral holes 11a, 11b for urine flow. The tubular membrane 2 has an enlargement in the form of a balloon 33 next to the distal part 3a of the inner tube 3. When the fluid is injected through the hole 13 of the handle 36, said enlargement of the tubular membrane 2 forms a balloon 33 at the end of the catheter 1, as a part of hermetically sealed space 14 which may be filled with fluid. Hole 13 of the handle 36 can be arranged on the distal part 36a of the handle 36, the medial part 36b of the handle 36 or on the proximal part 36c of the handle 36.

Figure 3:
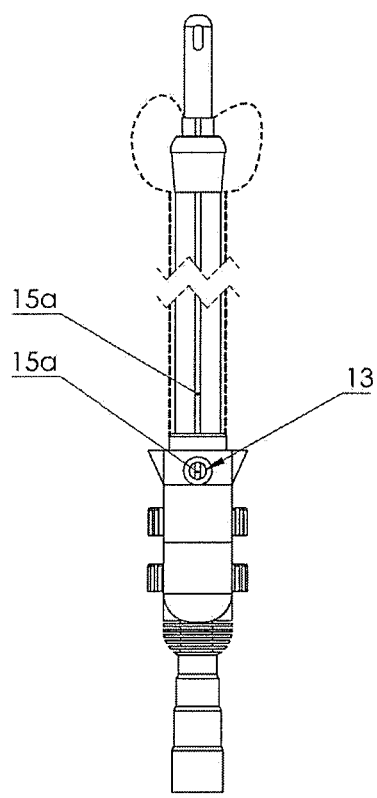
FIG. 3 is a view from the side of the catheter.

As shown in FIG. 3, the lateral channels 15a, 15b of the outer tube 4 must be placed in the position under the hole 13 of the handle 36, during the removal of the fluid from hermetically sealed space 14. The lateral channels 15a, 15b of the outer tube 4 are essential for efficient fluid flow from the balloon 33 through hole 13, when the hole 13 is located on the distal part 36a of the handle 36 or on the medial part 36b of the handle 36 during the removal of the fluid from the hermetically sealed space 14. Additionally, two lateral channels 19a, 19b of the inner tube 3 are essential for efficient fluid flow from the balloon 33 through hole 13, when the hole 13 is located on the proximal part 36c of the handle 36. This is important because the tubular membrane 2 should not get completely attached to the surface of the outer tube 4 which would block the flow of the fluid.

Figure 4:
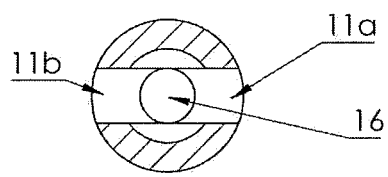
FIG. 4 is a transversal cross-sectional view along line B-B.
Figure 5:
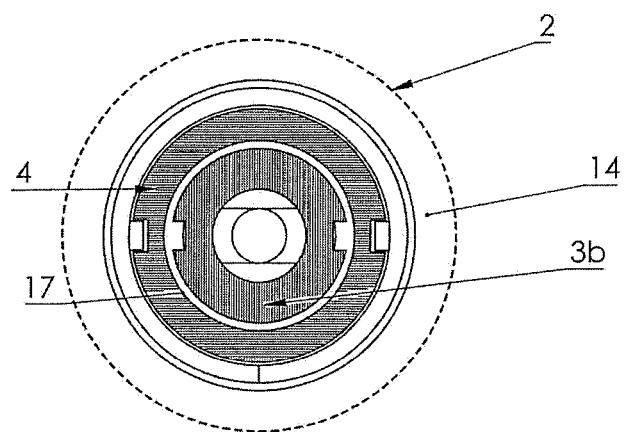
FIG. 5 is a transversal cross-sectional view along line C-C.
Figure 6:
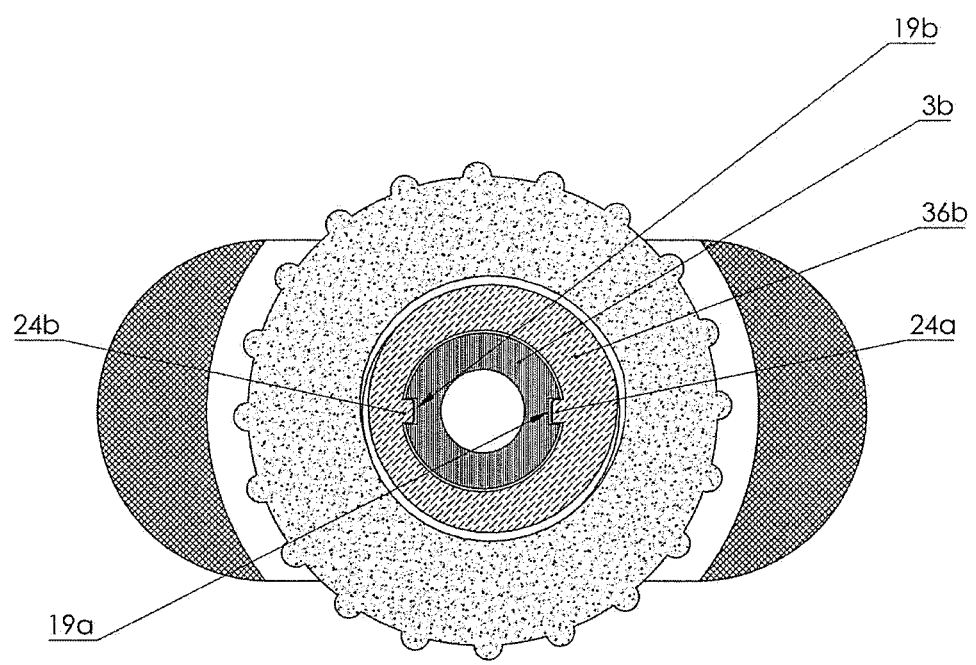
FIG. 6 is a transversal cross-sectional view along line D-D.
Figure 7:
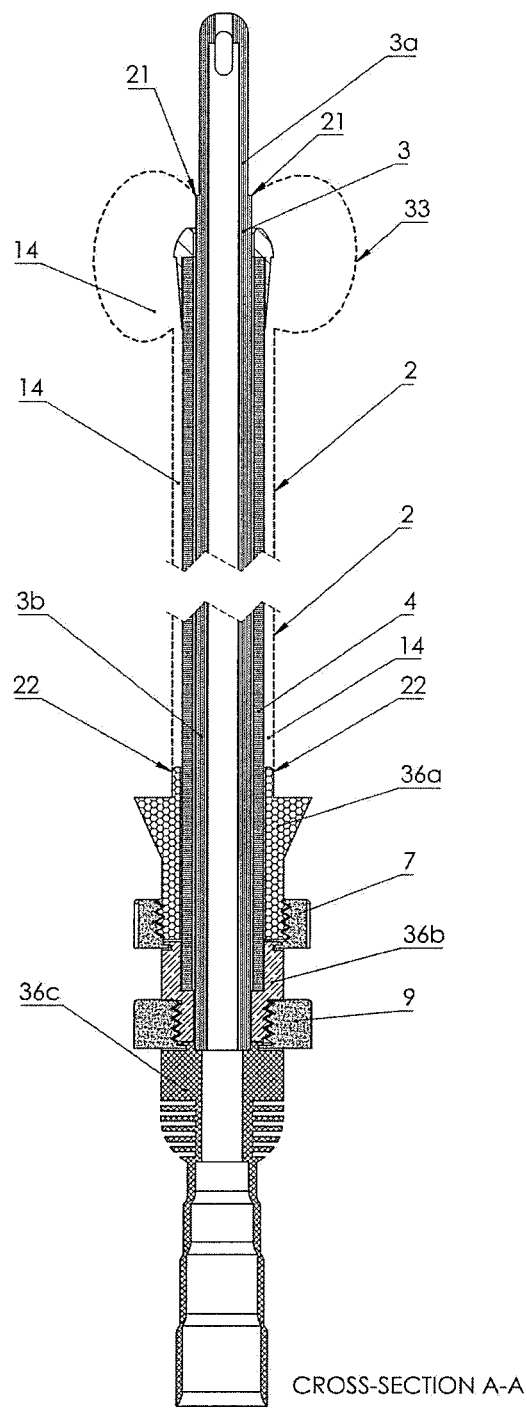
FIG. 7 is a longitudinal cross-sectional view along line A-A.

The distal part 3a of the inner tube 3 has a hole 16 at the end of distal part 3a of the inner tube 3 and two lateral holes 11a, 11b (FIG. 4). The distal part 3a of the inner tube 3 must have more than one hole, in order to prevent urine flow obstruction and pseudopolyps making. When catheter is placed within bladder, the lateral holes lateral holes 11a, 11b of the inner tube 3 should not be in contact with the membrane, because that would block urine flow through catheter.

In one embodiment, the hermetically sealed space 14 is inflated with fluid. This fluid layer between the outer tube 4 and tubular membrane 2 provides soft and smooth catheter surface in order to amortize the forces transmitted from the catheter to the epithelium and prevent biofilm making. Moreover, the fluid layer improves fitting of catheter to urethra surfaces and prevents side flow of urine between urethra walls and catheter. It is important to notice that inner lumen 17 of the outer tube 4 is circular, and body 3b of the inner tube 3 may easily slide through it.

The body 3b of the inner tube 3 can slide through medial part 36b of the handle 36, but rotatory movement is blocked because body 3b of the inner tube 3 has two lateral channels 19a, 19b that fit with protrusions 24a, 24b of the medial part 36b of the handle 36 thus preventing the rotation of inner tube 3.

The outer tube 4 is in fixed connection with the medial part 36b of the handle 36. Body 3b of the inner tube 3 is in fixed connection to the proximal part 36c of the handle 36.

Figures 11, 12, 13:
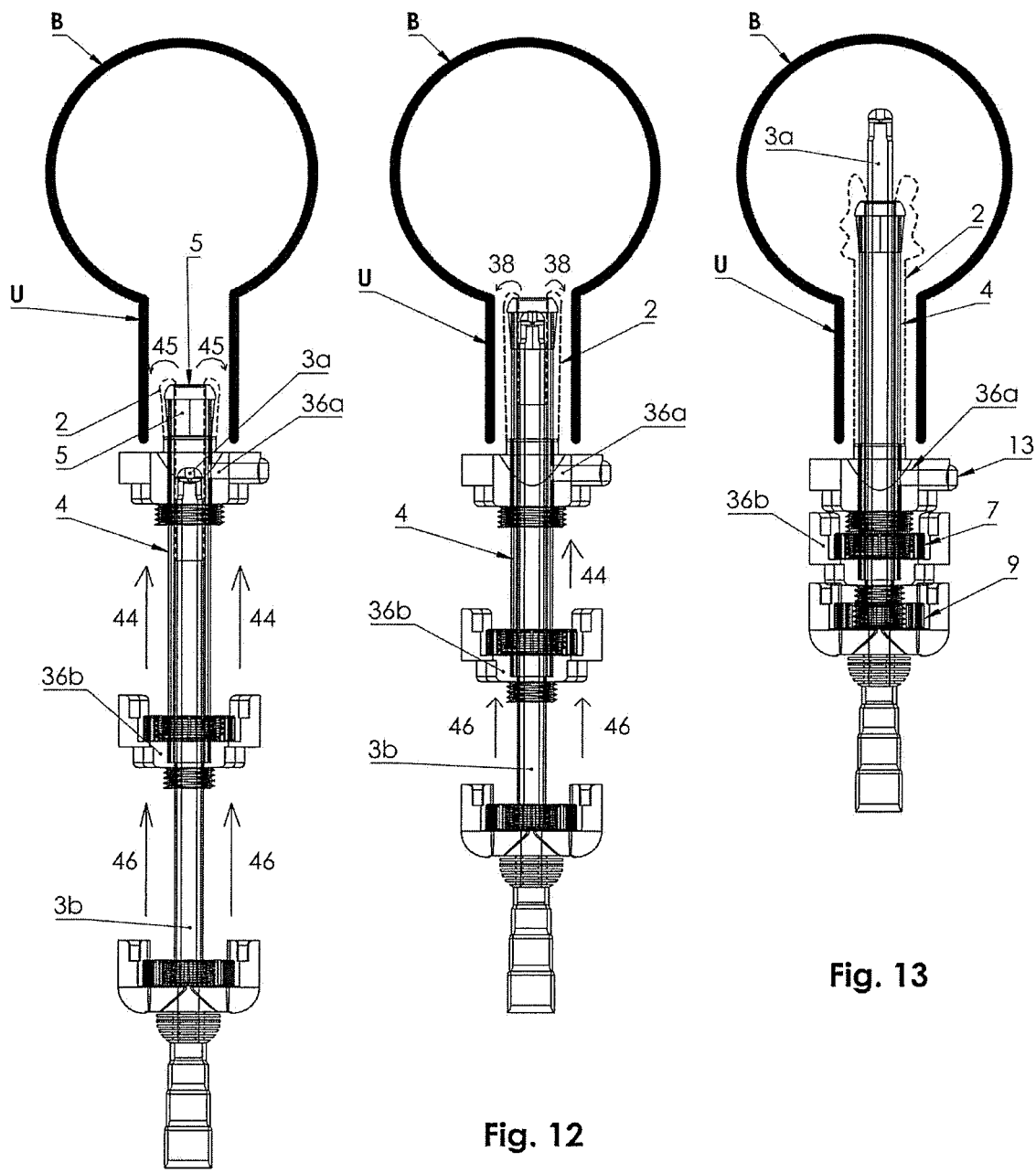
FIG. 11 shows the catheter with its internal parts prior to placement.
FIG. 12 shows the catheter with its internal parts during insertion through urethra into the urinary bladder.
FIG. 13 shows the catheter with its internal parts which is placed in the urinary bladder.

A distal membrane attachment 21 is placed between the body 3b of the inner tube 3 and the distal part 3a of the inner tube 3. The diameter of the distal part 3a of the inner tube 3 is smaller than the diameter of the body 3b of the inner tube 3. A proximal membrane attachment 22 is placed on the distal part 36a of the handle 36. It is important to notice that connections between distal part 36a of the handle 36, tubular membrane 2, body 3b of the inner tube 3 and proximal part 36c of the handle 36 are fixed and hermetically sealed. In cases of prolonged use, the catheter must be fixed in a way that allows positioning at the same place in the urethra for the prolonged period of time. When the catheter is placed in urinary bladder, as shown in FIGS. 13 and 14, the nut 7 of the medial part 36b of the handle 36 and the nut 9 of the proximal part 36c of the handle 36 are screwed, and proximal part 36c of the handle 36 is tightly engaged with the medial part 36b of the handle 36 and distal part 36a of the handle 36. As a result, the hermetically sealed space 14 is enclosed by surfaces of distal part 36a of the handle 36, tubular membrane 2, body 3b of the inner tube 3, proximal part 36c of the handle 36 and medial part 36b of the handle 36. Through the hole 13 of the distal part 36a of the handle 36 (shown in FIG. 3), fluid can be injected into hermetically sealed space 14 to expand the tubular membrane 2 having balloon 33 which holds the catheter in place for prolonged period of time.

Figure 8:
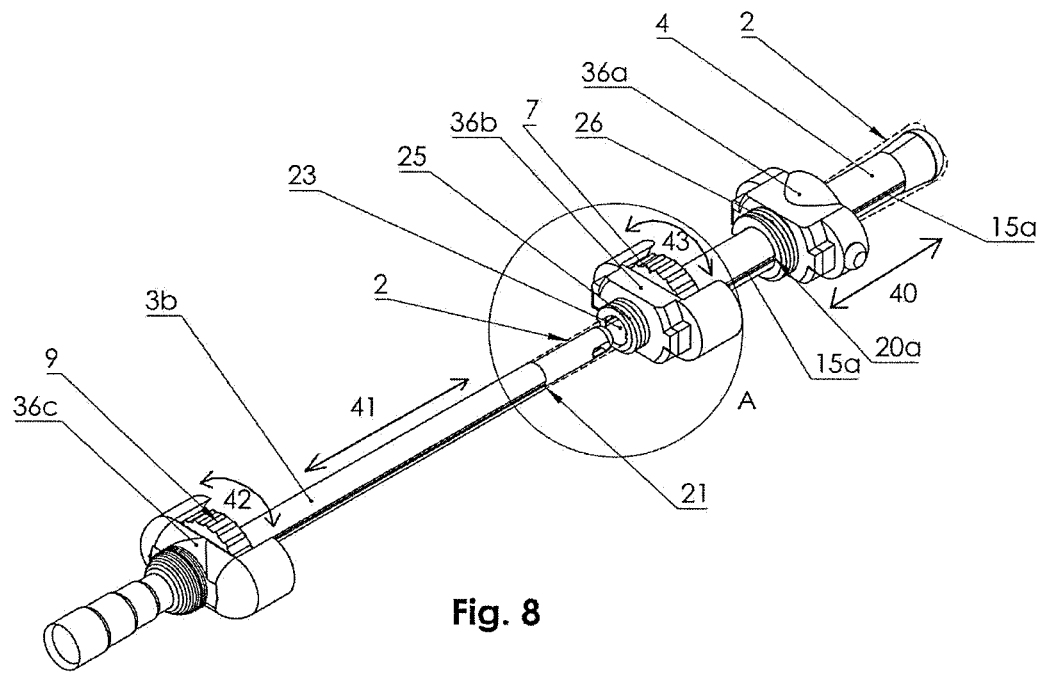
FIG. 8 is a perspective view of the catheter in a disassembled configuration.

The lateral channels 15a, 15b of the outer tube 4 fit with protrusions 20a, 20b of the distal part 36a of the handle 36, respectively, which allows sliding of the distal part 36a of the handle 36 along the outer tube 4, as shown by the arrow 40 in FIG. 8, without rotation around longitudinal axis of the outer tube 4.

Tubular membrane 2 from the distal membrane attachment 21 passes through the lumen 23 of the medial part 36b of the handle 36 and is attached to the distal part 36a of the handle 36.

Figure 9:
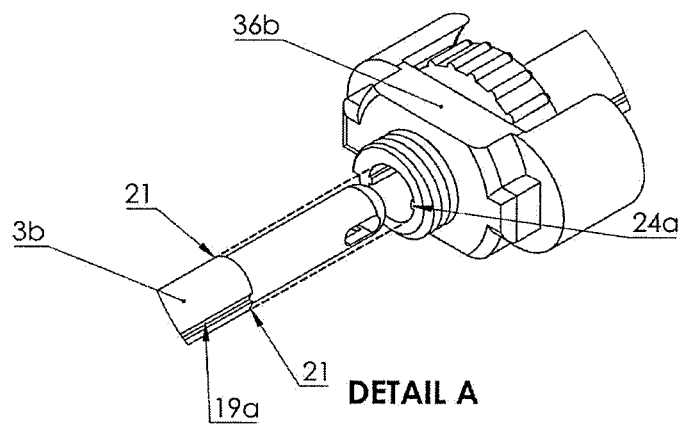
FIG. 9 is a view of detail A of the catheter.
Figure 10:
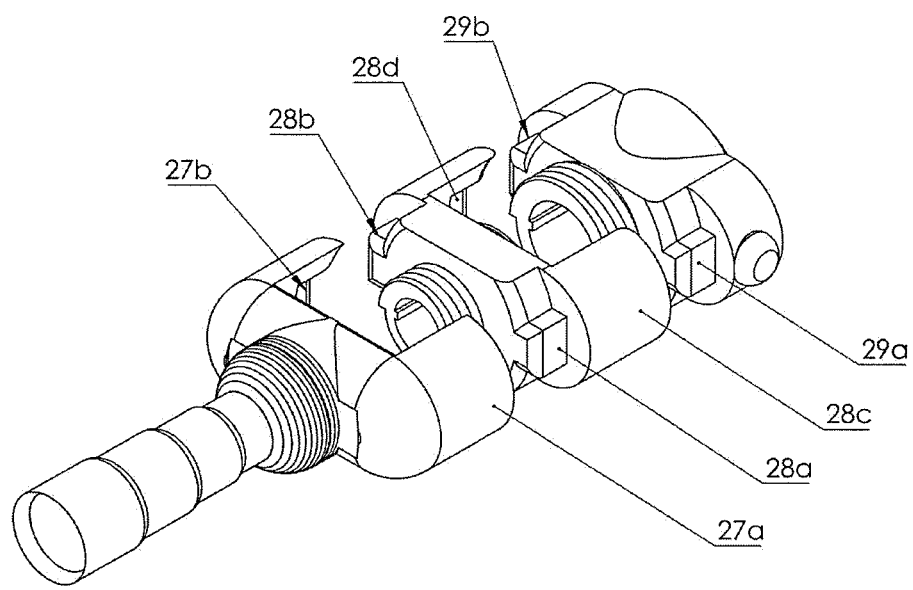
FIG. 10 is an exploded view of the proximal part, medial part and distal part of the handle.

As shown in FIG. 9, body 3b of the inner tube 3 contains lateral channels 19a, 19b of the inner tube 3 which fit with protrusions 24a, 24b of the medial part 36b of the handle 36, respectively. These "channels and protrusions", allow longitudinal sliding of the body 3b of the inner tube 3 as indicates an arrow 41 in FIG. 8. In addition, "channels and protrusions", prevent the rotational movement of the body 3b of the inner tube 3.

It is important to note that theet 20a, 20b are positioned on the distal part 36a of the handle 36, while theet 24a, 24b are positioned on the medial part 36b of the handle 36.

Proximal part 36c of the handle 36 contains the nut 9 which fits with thread 25 of the medial part 36b of the handle 36 and forms hermetically fitted junction between these two parts. The nut 9 of the proximal part 36c of the handle 36, can freely rotate in the direction as shown by the arrow 42 in FIG. 8. This provides tight engagement between proximal part 36c of the handle 36 and medial part 36b of the handle 36.

Similarly, the nut 7 of the medial part 36b of the handle 36, is freely rotatable in the direction as shown by the arrow 43 in FIG. 8, and fits with a thread 26 of the distal part 36a of the handle 36 thus providing tight engagement between medial part 36b of the handle 36 and the distal part 36a of the handle 36.

Tight engagements of the lateral parts are important for prevention of twisting of the catheter during nuts screwing. Thus, lateral parts 27a, 27b of the proximal part 36c of the handle 36 fit with lateral parts 28a, 28b of medial part 36b of the handle 36, respectively, and lateral parts 28c, 28d of medial part 36b of the handle 36 fit with lateral parts 29a, 29b of distal part 36a of the handle 36, respectively. This prevents rotation of the proximal part 36c, medial part 36b and distal part 36a of the handle 36 during rotation of the nuts 7, 9.

As shown in FIG. 11, prior to placement of the catheter 1, tubular membrane 2 and distal part 3a of the inner tube 3, i.e. the parts of the catheter 1 that are in direct contact with urethra and urinary bladder, are protected from the contamination with bacteria from external environment, by being enclosed inside the outer tube 4. This prevents contamination of these parts during preparation of the catheter insertion (hygienic procedures). The catheter 1, according to the present invention, can simply be operated with one hand of the medical practitioner placed on distal part 36a of the handle 36 as well as on the tissue which surrounds the meatus of the urethra, while the other hand is used to push the medial part 36b of the handle 36 or the outer tube 4. As pressure is applied in the direction as indicated by the arrow 44 as shown in FIG. 11, the forward end of the tubular membrane 2 unrolls progressively in the direction as indicated by the arrow 45 as shown in FIG. 11 to cover the walls of the urethra U. This "eversible" principle of motion of tubular membrane 2 during catheter 1 insertion prevents transport of bacteria from the region around the meatus of urethra and distal part of urethra to urinary bladder, but also reduces sliding friction, pain and trauma of epithelium of the urethra.

During unrolling in the direction as indicated by the arrow 45 as shown in FIG. 11, the tubular membrane 2 pulls the body 3b of the inner tube 3 through the outer tube 4 as indicated by the arrow 46 as shown in FIG. 12.

As shown in FIG. 13, the lengths of the body 3b of the inner tube 3, the outer tube 4 and tubular membrane 2 are sufficient to allow the tubular membrane 2 to cover the walls of the urethra and distal part 3a of inner tube 3 to enter the bladder.

When the catheter is placed in urinary bladder, as shown in FIG. 13, the nut 7 of the medial part 36b of the handle 36 and the nut 9 of the proximal part 36c of the handle 36 provide tight engagement between proximal part 36c, medial part 36b and distal part 36a of the handle 36. The proximal part 36c of the handle 36 is than tightly engaged with the medial part 36b of the handle 36, and medial part 36b of the handle 36 is tightly engaged with distal part 36a of the handle 36. The tubular membrane 2 encloses the hermetically sealed space 14.

Prior to removal of the catheter 1 from the urinary bladder, the medical practitioner must remove the fluid from the hermetically sealed space 14 through the hole 13, followed by unscrewing the nut 7 of the medial part 36b of the handle 36 and nut 9 of the proximal part 36c of the handle 36. As a result, the balloon 33 collapses allowing the catheter 1 to be removed (FIG. 15).

During the removal of the catheter 1, the medical practitioner can easily use the catheter 1 only by one hand holding medial part 36b of the handle 36, while the other hand may pull proximal part 36c of the handle 36 or body 3b of the inner tube 3, in the direction as indicated by the arrow 47 as shown in FIG. 16. By pulling of the inner tube 3, the tubular membrane 2 is drawn together with the exhausted balloon 33 in the direction as indicated by arrows 48 and 49 as shown in FIG. 16. In turn, the tubular membrane progressively uncovers the walls of the urethra, and the outer tube 4 moves in the direction as indicated by the arrow 50 (FIG. 16). During this movement, sliding friction between tubular membrane 2 and urethra is reduced. It is important to notice that this kind of catheter 1 removal prevents the urethral damage usually caused by an incomplete collapse of the balloon. As already noted in the prior art, an incomplete collapse of the balloon, also known as a "creep phenomenon" of indwelling catheters, damages the urethra. Overcoming this problem allows also the suprapubic use of catheter 1 according to the present invention.

Figure 17:
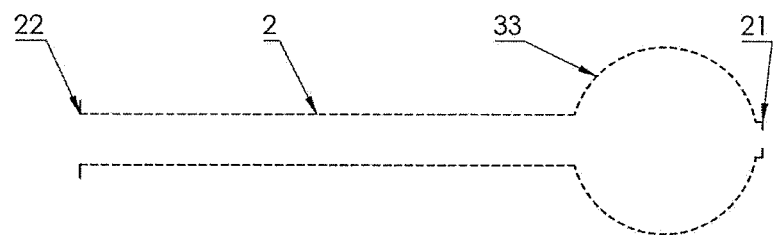
FIG. 17 is a tubular membrane with an enlargement of the tubular membrane in the form of a balloon.
Figure 18:
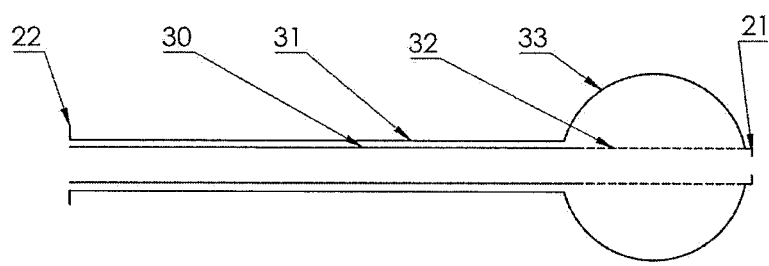
FIG. 18 is a modification 1 of the tubular membrane.
Figure 19:
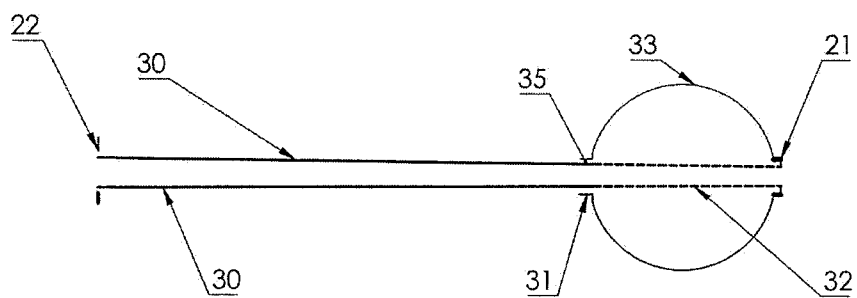
FIG. 19 is a modification 2 of the tubular membrane.
Figure 20:
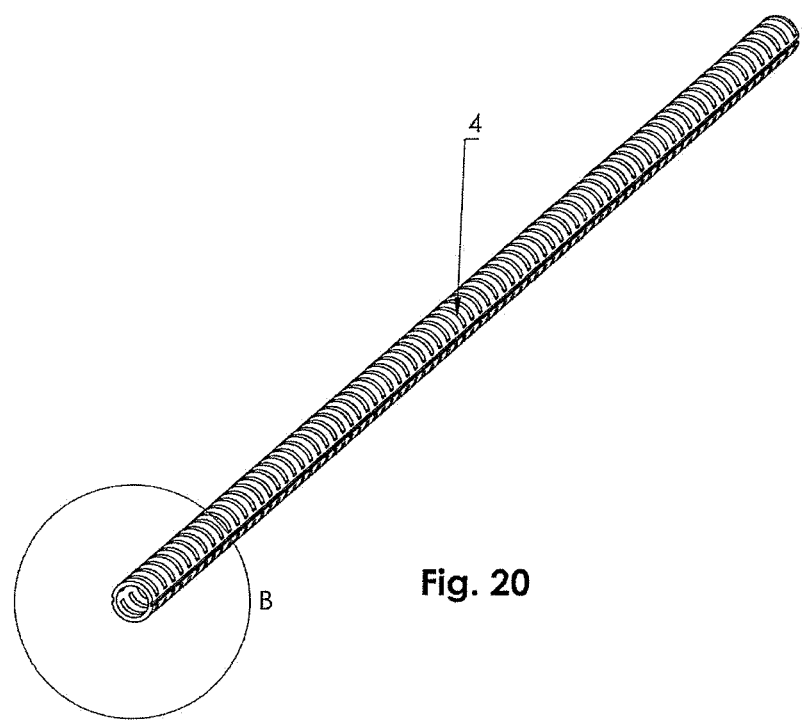
FIG. 20 is a perspective view of the modification 1 of the outer tube.

The tubular membrane 2 should be made from material with ultrahigh strength characteristic, thin walls and compliance range from 0% to 10%. Preferably, the tubular membrane 2 is coated. FIG. 17 shows distal membrane attachment 21 and proximal membrane attachment 22. The balloon 33 may vary in shape, size, position and number.

In one embodiment, (Modification 1 of the tubular membrane 2) the tubular membrane 2 is made of two layers. The Inner layer 30 of the tubular membrane 2 is made from material with ultrahigh strength characteristic and low friction rate, thin walls and compliance range from 0% to 10%. The outer layer 31 of tubular membrane 2 is made from elastic material suitable for use in the direct contact with human tissues. These two layers are in connection between distal membrane attachment 21 and proximal membrane attachment 22. In addition, they are tightly engaged along their entire length, except within the balloon 33 where they are apart from each other. The inner layer 30 of tubular membrane 2 contains holes 32 within the balloon 33. Thus, fluid can flow through the holes 32 in both directions, allowing inflating and exhausting the balloon 33.

In another embodiment, (Modification 2 of the tubular membrane 2) the inner layer 30 of the tubular membrane 2 and the outer layer 31 of tubular membrane 2 are positioned only within the balloon 33. The inner layer 30 of tubular membrane 2 is connected with outer layer 31 of tubular membrane 2 by the tight attachment 35 and distal membrane attachment 21. Inner layer 30 of tubular membrane 2 contains holes 32 within the balloon 33 and fluid can flow through these holes 32 in both directions this enabling the inflating or exhausting the balloon 33.

Figure 21:
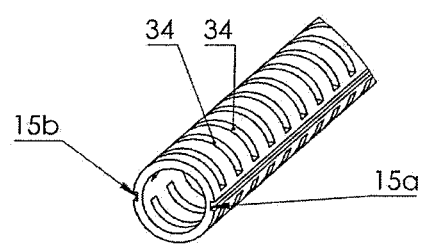
FIG. 21 shows the detail B of modification 1 of the outer tube.

In another embodiment, (Modification 1 of the outer tube 4), the outer tube 4 contains apertures 34 of different shapes, which provide flexibility of the tube. Size, shape, position and number of these apertures 34 can be different to ensure flexibility and prevent twisting. Detail B view of the outer tube 4 containing apertures 34 along the walls of the outer tube 4 having lateral channels 15a, 15b of the outer tube 4 is presented in FIG. 21.

The invention claimed is:

1. A catheter comprising a handle having a hole, a tubular membrane having a part which is partially enlarged for forming a balloon, inner tube being attached to the handle, the inner tube having a body and a distal part, the distal part containing lateral holes, and an outer tube having a rounded tip, wherein a proximal opening of the catheter is attachable to a bag for holding body fluids wherein the handle comprises a proximal part of the handle a medial part of the handle and a distal part of the handle, wherein the proximal part of the handle is detachably connected with the medial part of the handle and medial part of the handle is detachably connected with the distal part of the handle, the medial part of the handle further comprising a first nut, said first nut fitting with a thread of the distal part of the handle, and the proximal part of the handle comprising a second nut, said second nut fitting with a thread of the medial part of the handle, the tubular membrane being slidable between the distal part of the handle and the distal part of the inner tube through the outer tube, the outer tube is in fixed connection to the medial part of the handle and the body of the inner tube is mounted to the proximal part of the handle, the distal part of the handle further comprising a proximal membrane attachment, the inner tube further comprising a distal membrane attachment coupling structurally configured to provide for tight engagement of the tubular membrane with the distal part of the inner tube, a diameter of the distal part of the inner tube being smaller than a diameter of the body of the inner tube, the outer tube further having lateral channels fitting with protrusions of the distal part of the handle, respectively, for sliding of the distal part of the handle along the outer tube, the body of the inner tube having lateral channels fitting with protrusions of the medial part of the handle, respectively, said distal part of the inner tube having a lumen at the end of the distal part of the inner tube and two lateral holes; and wherein a hermetically sealed space is formed between the outer tube and the tubular membrane.

2. The catheter according to patent claim 1, wherein the tubular membrane and distal part of the inner tube are enclosed inside the outer tube.

3. The catheter according to claim 1, wherein the first nut of the medial part of the handle and second nut of the proximal part of the handle are configured to be tightly engaged and to join the proximal part of the handle, the medial part of the handle and the distal part of the handle.

4. The catheter according to claim 1, wherein the hermetically sealed space is inflated with fluid by injection of the fluid through the hole of the handle and a diameter of hermetically sealed space is larger than a diameter of the rounded tip of the outer tube.

5. The catheter according to claim 1, wherein the hole of the handle is arranged on the distal part of the handle or on the medial part of the handle or on the proximal part of the handle.

6. The catheter according to claim 1, wherein the tubular membrane contains an inner layer and an outer layer.

7. The catheter according to claim 6, wherein the inner layer and the outer layer are engaged by the distal membrane attachment coupling and the proximal membrane attachment and are also tightly engaged between themselves along their entire length, except within the balloon where they are apart from each other.

8. The catheter according to claim 6, wherein the inner layer of tubular membrane contains holes within the balloon.

9. The catheter according to claim 6, wherein the balloon encloses the tubular membrane containing the inner layer and the outer layer.

10. The catheter according to claim 6, wherein the inner layer of tubular membrane is connected with the outer layer of tubular membrane by a proximal attachment coupling and the distal membrane attachment coupling.

11. The catheter according to claim 1, wherein the outer tube contains apertures.

* * * * *